United States Patent
Kelly et al.

(10) Patent No.: US 7,242,979 B1
(45) Date of Patent: Jul. 10, 2007

(54) EXTERNAL DEFIBRILLATOR AND METHODS FOR OPERATING THE EXTERNAL DEFIBRILLATOR

(75) Inventors: Patrick F. Kelly, Edmonds, WA (US); Gregory T. Kavounas, Kirkland, WA (US); Joseph L. Sullivan, Kirkland, WA (US)

(73) Assignee: MedTronic Physio-Control Manufacturing Corporation, Redmond, WA (US)

( * ) Notice: Subject to any disclaimer, the term of this patent is extended or adjusted under 35 U.S.C. 154(b) by 459 days.

(21) Appl. No.: 10/622,868

(22) Filed: Jul. 17, 2003

Related U.S. Application Data

(60) Provisional application No. 60/412,340, filed on Sep. 20, 2002.

(51) Int. Cl.
*A61N 1/365* (2006.01)
(52) U.S. Cl. .................... 607/5; 607/6; 607/7
(58) Field of Classification Search ............... 607/5–7, 607/62
See application file for complete search history.

(56) References Cited

U.S. PATENT DOCUMENTS

| | | | |
|---|---|---|---|
| 5,607,454 A | 3/1997 | Cameron et al. | |
| 5,797,969 A | 8/1998 | Olsen et al. | |
| 5,803,927 A * | 9/1998 | Cameron et al. | 607/5 |
| 6,029,085 A | 2/2000 | Olsen et al. | |
| 6,553,251 B1 | 4/2003 | Lahdesmaki | |

OTHER PUBLICATIONS

U.S. Appl. No. 11/008,876, filed on Dec. 9, 2004, entitled "External Defibrillator with charge advisory algorithm".

* cited by examiner

*Primary Examiner*—Carl Layno
*Assistant Examiner*—Eric D. Bertram

(57) ABSTRACT

Methods and apparatus are provided for minimizing the inherent time delays within external defibrillators. The methods and apparatuses utilize timing schemes for initiation and completion of charging of an energy storage device of an external defibrillator, measuring one or physical parameters of the patient and conducting a physiology analysis of the patient. The initiation and completion of one or more of these activities are arranged so that the energy storage device is charged to a desired level and available for a defibrillation shock to the patient with minimal delay after activation of the external defibrillator.

35 Claims, 8 Drawing Sheets

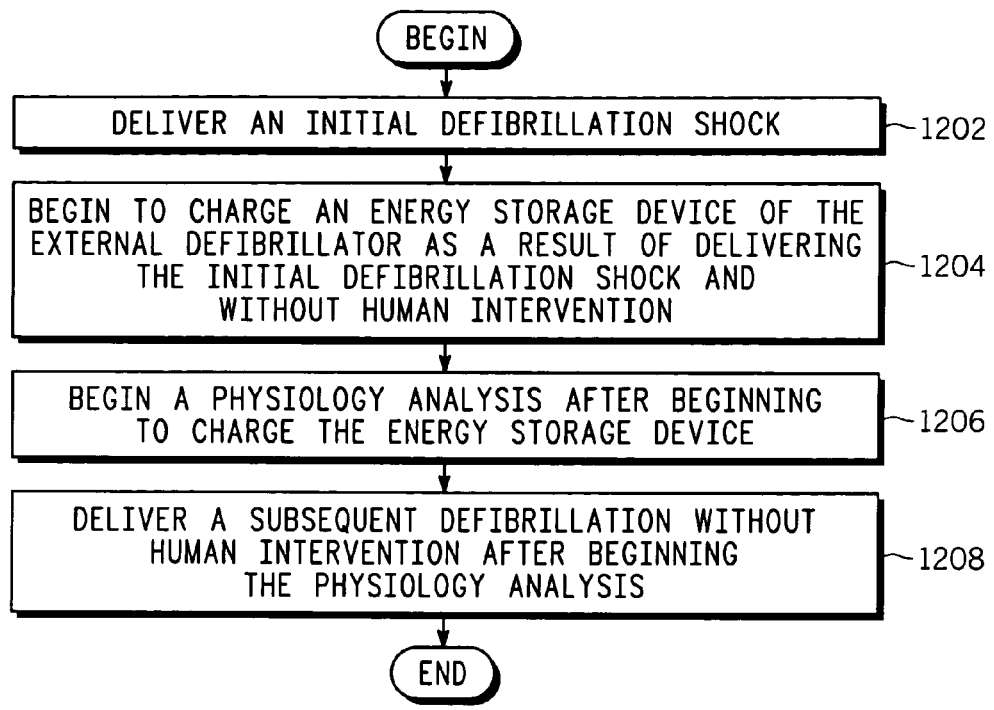
FIG. 12  1200
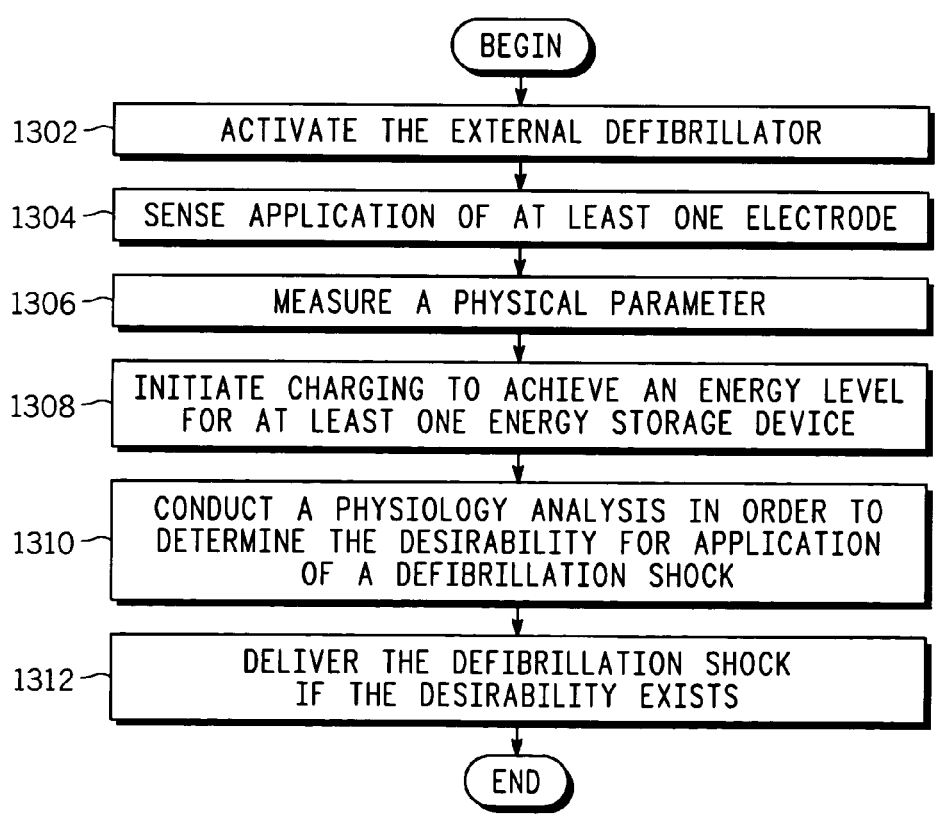
1300  FIG. 13

EXTERNAL DEFIBRILLATOR AND METHODS FOR OPERATING THE EXTERNAL DEFIBRILLATOR

CROSS-REFERENCES TO RELATED APPLICATIONS

This application claims the benefit of U.S. Provisional Application No. 60/412,340, filed Sep. 20, 2002.

TECHNICAL FIELD

The present invention generally relates to charging, and more particularly relates to an external defibrillator and methods of operating the external defibrillator.

BACKGROUND

A normal human heart pumping pattern is called a sinus rhythm, and is regulated by the body's biological pacemaker within the upper right chamber of the heart, which is commonly referred to as the right atrium. This natural pacemaker, which is generally referred to as the sinoatrial (SA) node, sends electrical signals to the right and left ventricular muscles in the lower chambers of the heart. The ventricular muscles then implement the pumping action under control of the SA node. The right ventricular muscle pumps blood to the lungs for oxygenation, and the left ventricular muscle pumps the oxygenated blood to various parts of the body.

In certain circumstances, the normal or sinus heartbeat rhythm may be adversely affected as a result of some type of malfunction in the heart's electrical control system. When this type of malfunction occurs, an irregular heartbeat may result, causing the ventricular muscles to pump ineffectively, thus reducing the amount of blood pumped to the body. This irregular heartbeat is generally referred to as an arrhythmia.

A particularly serious arrhythmia is known as Ventricular Fibrillation (VF), which is a malfunction characterized by rapid, uncoordinated cardiac movements replacing the normal contractions of the ventricular muscles. In this event, the ventricular muscles are not able to pump blood out of the heart, and there is no initiation of a heartbeat. VF rarely terminates spontaneously, and is therefore a leading cause of sudden cardiac death. The unpredictability of VF and other irregular heat beat conditions exacerbates the problem, and emphasizes the need for early therapeutic intervention to prevent the loss of life.

Defibrillators are devices for providing life-saving electrical shock therapy to persons experiencing an irregular heat beat, such as VF. A defibrillator provides an electrical shock to the heart, in order to convert the irregular heat beat to a normal sinus rhythm. One type of defibrillator is surgically implanted in patients who are considered likely to need electrical shock therapy, precluding the necessity of constant monitoring by medical personnel.

A more commonly used type of defibrillator is the external defibrillator, which sends electrical shock pulses to the patient's heart through external electrodes applied to the patient's chest. External defibrillators may be manually operated, as are typically used in hospitals by medical personnel or may be semi-automatic, semi-automated, fully automatic, or fully automated devices, where they can be used in any location where an unanticipated need may occur.

It is well known that time is an important factor in the successful application of electrical shock therapy. According to recent data, the survival rate of persons suffering from ventricular fibrillation decreases by about ten percent (10%) for each minute the administration of a defibrillation shock is delayed. It is therefore desirable to minimize the time duration between powering up an external defibrillator and administering the electrical shock therapy to the patient.

Prior to delivery of the defibrillation shock, the defibrillator electrodes are attached to the patient, the patient's condition and parameters are measured and analyzed, and a shock energy circuit is charged to an appropriate level. One or more of these activities can be done by medical/emergency personnel, as in the case of manual defibrillators, or by an automatic or automated process, as in the case of automatic, semi-automatic, automated and semi-automated defibrillators. These actions are disadvantageously time-consuming, and delay the administration of the shock therapy.

Accordingly, it is desirable to reduce the inherent time delays associated with shock administration in external defibrillators. In addition, it is desirable to implement delay reductions in all types of external defibrillators, including fully automatic, semi-automatic, fully automated or semi-automated and manual defibrillators. Furthermore, other desirable features and characteristics of the present invention will become apparent from the subsequent detailed description of the invention and the appended claims, taken in conjunction with the accompanying drawings and this background of the invention.

BRIEF DESCRIPTION OF THE DRAWINGS

The present invention will hereinafter be described in conjunction with the following drawing figures, wherein like numerals denote like elements.

FIG. 12 is a flowchart for operating the external defibrillator of FIG. 2 in accordance with a sixth exemplary embodiment of the present invention; and FIG. 13 is a flowchart for operating the external defibrillator of FIG. 2 in accordance with a seventh exemplary embodiment of the present invention.

DETAILED DESCRIPTION

The following detailed description of the invention is merely exemplary in nature and is not intended to limit the invention or the application and uses of the invention. Furthermore, there is no intention to be bound by any expressed or implied theory presented in the preceding background of the invention or the following detailed description of the invention.

Figure 1:
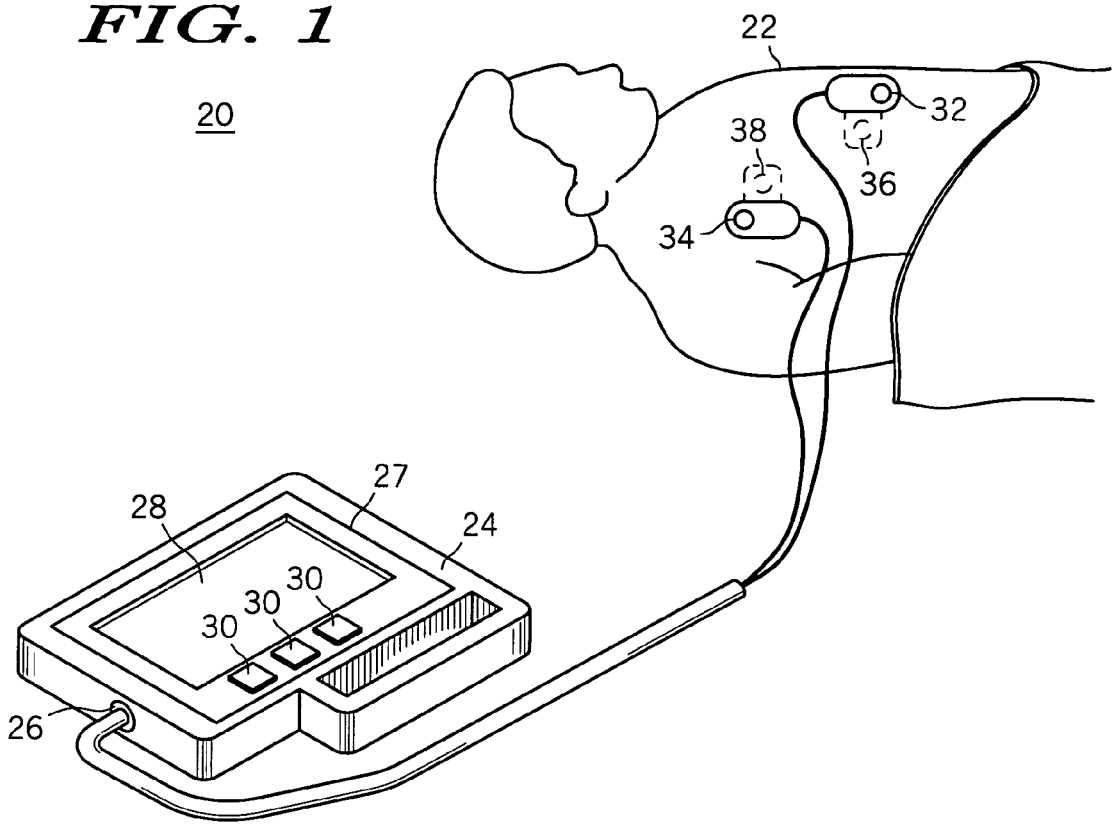
FIG. 1 is an illustration of an external defibrillator system connected to a patient in accordance with an exemplary embodiment of the present invention.

FIG. 1 is a defibrillator system 20 that is configured to deliver a defibrillation shock to a patient 22, such as a victim of VF. The defibrillator system 20, includes, but is not limited to, an external defibrillator 24 having a connection port 26 that is configured to receive one or more electrodes (32,34). The external defibrillator 24 can be any number of external defibrillators in accordance with the present invention. For example, the external defibrillator 24 can be an Automatic External Defibrillator or Automated External Defibrillator (AED), semi-Automatic or semi-Automated External Defibrillator, or a manually operated external defibrillator. As used herein, an automatic or automated activity occurs without human intervention. While many of the exemplary embodiments of the invention apply to all types of external defibrillators, some of the embodiments are only for specific types, such as embodiments only for manual defibrillators, only for automated, or only for semi-automated.

The external defibrillator 24 preferably includes a user interface 27 having a display 28 that is configured to visually present various measured or calculated parameters of patient 22 and/or other information to the operator (not shown) of the external defibrillator 24. For example, the display 28 can be configured to visually present the transthoracic impedance, ElectroCardioGram (ECG) and/or other physiology signals of the patient. The user interface 27 can also include one or more input devices (e.g., switches or buttons) 30 that are configured to receive commands or information from the operator. The external defibrillator 24 is configured generate a charge that is delivered to the patient 22 as the defibrillation shock with one or more electrodes (32, 34).

The one or more electrodes (32, 34) and/or one or more sensing electrodes (36, 38) are also configured to sense one or more physiology and/or physical parameters of the patient 22 that are received by the external defibrillator 24 at the connection port 26. The signals provided by the one more electrodes (32,34) and/or one more sensing electrodes (36, 38) are preferably evaluated by the external defibrillator 24 to determine, among other things, whether a defibrillation shock should be applied to patient 22 in accordance with techniques known to those of ordinary skill in the art. This external defibrillator 24 can also evaluate the signals provided by the one more electrodes (32,34) and/or one more sensing electrodes (36,38) to determination the waveform parameters of the defibrillation shock (e.g., sinusoidal, monophasic, biphasic, truncated) as well as magnitude and duration.

Figure 2:
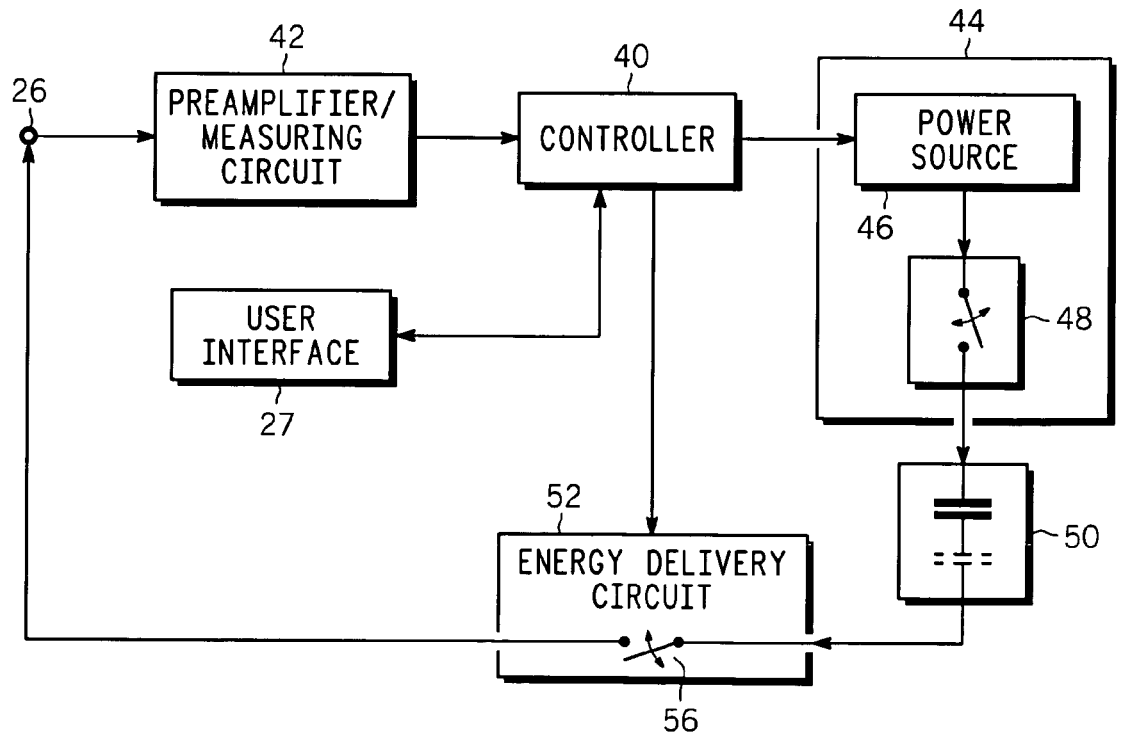
FIG. 2 is a simplified block diagram of an external defibrillator in accordance with a first exemplary embodiment of the invention.

Referring to FIG. 2, a simplified block diagram of the external defibrillator 24 is illustrated in accordance with an exemplary embodiment of the present invention. The external defibrillator 24 preferably includes a controller 40, the user interface 27 (e.g., switches or buttons 30 and/or display 28 as shown in FIG. 1), a pre-amplifier/measuring circuit 42, a charging mechanism 44 that can include a power source 46 and a switch 48 to couple the power source 46 to the one or more energy storage devices (e.g., capacitors) 50 and an energy delivery circuit 52, which is illustrated as a switch 56 that is configured to selectively couple the one or more energy storage devices 50 to the connection port 26 under the control of the controller 40. The energy delivery circuit 52 can be implemented with any number of circuit configurations. For example, in a biphasic circuit, an H-bridge circuit can be used in accordance with the present invention. The controller 40 can be a single processing unit or multiple processing units and can be implemented with software, hardware, or a combination of hardware and software. The controller 40 is configured to at least partially control the operation of the external defibrillator 24, including control of charging the one or more energy storage devices 50.

Figure 3:
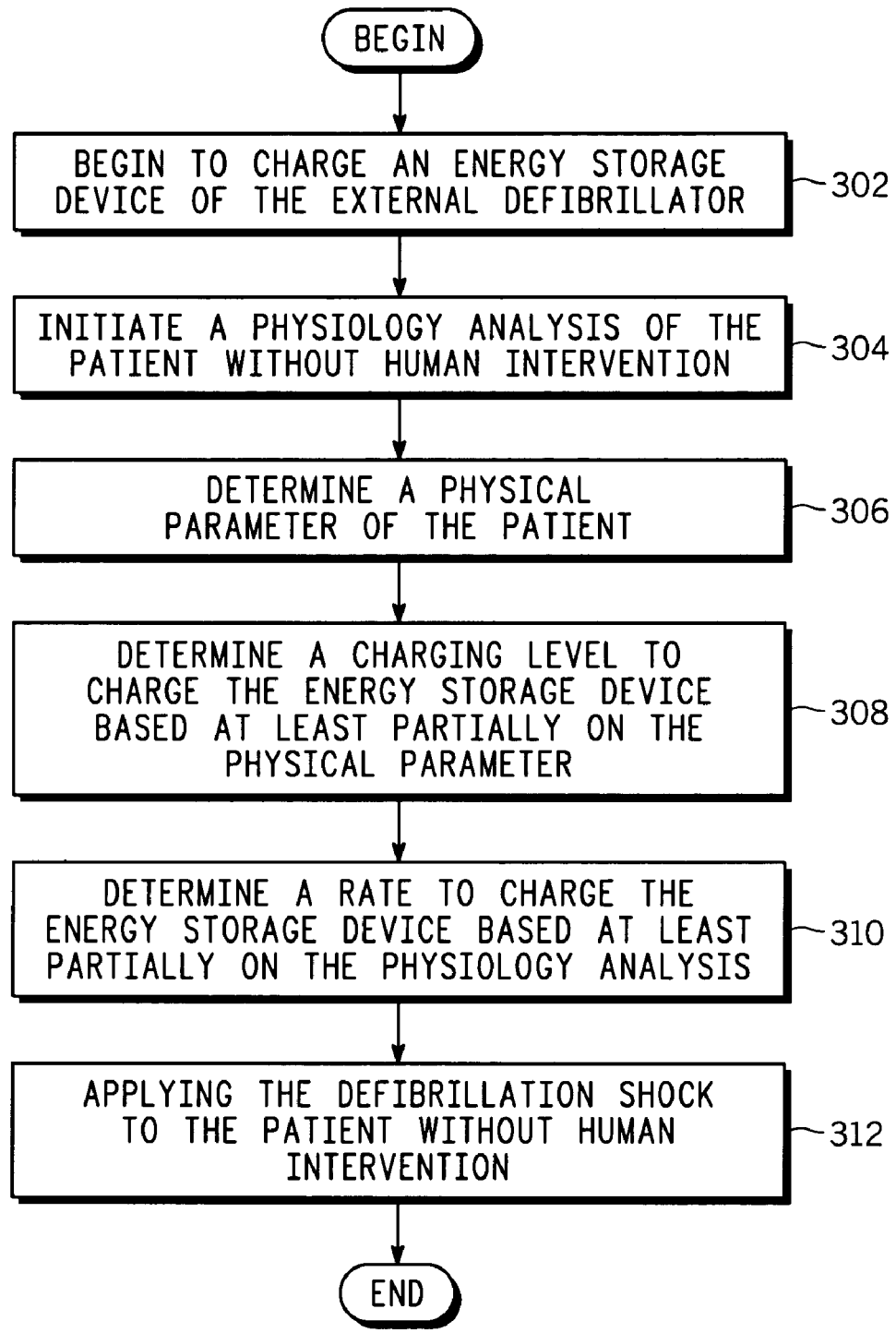
FIG. 3 is a flowchart for the method of operating the external defibrillator of FIG. 2 in accordance with a first exemplary embodiment of the present invention.

Referring to FIG. 3, a flowchart is presented that illustrates a method 300 of operating the external defibrillator of FIG. 2 in accordance with a first exemplary embodiment of the present invention. The method 300 begins with the charging of one or more energy storage devices of the external defibrillator 302. After beginning to charge the one or more energy storage devices 302, a physiology analysis of the patient is initiated without human intervention (i.e., an automatic or automated activity) 304. A physical parameter of the patient is determined 306 and a charging level is determined based at least partially on the physical parameter 308. In addition, a rate to charge the energy storage device is determined based at least partially on the physiology analysis 310 and the defibrillation shock is applied to the patient without human intervention 312.

Figure 4:
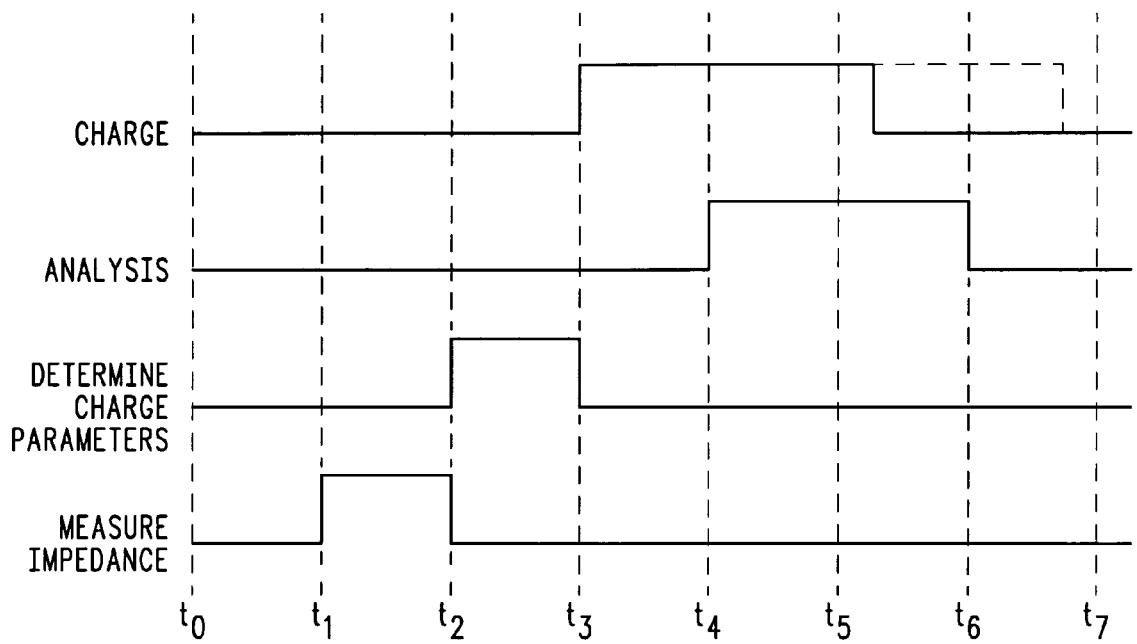
FIG. 4 is an exemplary timing diagram for operating the external defibrillator of FIG. 2 in accordance with the first exemplary embodiment of the present invention.

Referring to FIG. 4, a timing diagram 54 is presented that illustrates an example with greater detail for the operating of the external defibrillator in accordance with the first exemplary embodiment illustrated in FIG. 3. While the events presented in the timing diagram are shown as beginning and ending at the same time instant, it should be appreciated that delays can exist and the events do not need to begin and end at the same time instant as illustrated in FIG. 4. Rather, one event can end before or after another time event.

The external defibrillator 24 is activated at an initial time instant ($t_0$). This activation can be accomplished using any number of techniques such activation of an input switch 30 as shown in FIG. 1. After activation of the external defibrillator 24 at the initial time instant ($t_0$), one or more physical parameters of the patient are measured with the one or more of the electrodes (32,34,36,38) at a first time instant ($t_1$). Any number of physical parameters can be measured in accordance with the present invention. For example, the physical parameter can be the transthoracic impedance between at least two of the electrodes (32,34,36,38). The signal or signals associated with the one or more physical parameters are preferably provided to the pre-amplifier/measuring circuit 42 for preprocessing and/or amplification. The controller 40 receives the physical parameter and determines one or more charging parameters beginning at a second time instant ($t_2$). One of the charging parameters determined by the controller 40, which is at least partially based upon the physical parameter, is a charge for the one or more energy storage devices 50 that provides the desired defibrillation shock for the patient. This determination can be accomplished using any number of techniques known to those of ordinary skill in the art. The one or more energy storage devices 50 can be charged at any suitable rate, including, but not limited to fixed or preset charging rates, computed charging rates, rates that can be adjusted prior to and/or during charging based upon any number of factors such as the results of a physiology analysis. In addition, the charging of the one or more energy storage devices 50 can be accomplished using any number of charging apparatuses (e.g., one or more charging circuits) that are preferably controlled by the controller 40.

In addition to determining the charge, the controller 40 also preferably determines a charging rate to substantially achieve the charge no less than about a fifth time instant ($t_5$) prior to completion of a physiology analysis at a sixth time instant ($t_6$), which preferably began at a fourth time instant ($t_4$). In addition, the controller 40 also preferably determines the charging rate to substantially achieve the charge no more than about a seventh time instant ($t_7$) after completion of the physiology analysis at the sixth time instant ($t_6$). The charging rate can be determined using any number of techniques. For example the charging rate ($Q_{Rate}$) can be determined as follows:

$$Q_{Rate} = (Q_{Initial} - Q_{final})/\text{Time}_{Analysis} \quad (1)$$

Where $Q_{Initial}$ is magnitude of the initial charge when charging begins, $Q_{final}$ is magnitude of the final charge (i.e., the charge for the one or more energy storage devices 50 that provides the desired defibrillation shock for the patient) and $\text{Time}_{Analysis}$ is the time it takes to complete the physiology analysis, which can be the minimum time, maximum time, or average time to complete the physiology analysis. The minimum time, maximum time or average time will vary depending upon the measurement scheme and physiology analysis conducted by the controller 40. The physiology analysis can be any number analyses used to determine whether a defibrillation shock is preferably applied to the patient. For example, an ECG analysis can be conducted in accordance with techniques known to those of ordinary skill in the art based at least partially upon an ECG signal received by the controller 40 from the preamplifier/measuring circuit 42.

After the physiology analysis and the charge is substantially completed, which is no later than the seventh time instant ($t_7$) as previously described in this detailed description, and if the physiology analysis indicates it is appropriate to provide a defibrillation shock to the patient, the controller 40 can be configured to automatically initiate the appropriate action(s) to couple the one or more charged energy storage device(s) 50 to the patient and/or the controller 40 can request an operator request prior to initiating the appropriate action(s) to couple the one or more charged energy storage device(s) 50 to the patient. For example, the appropriate action(s) initiated by the controller 40 to couple the one or more charged energy storage device(s) to the patient can including closing a switch 56 of the energy delivery circuit 52 to couple the one or more energy storage devices 50 to two or more of the electrodes attached to the patient.

In accordance with the present invention, the controller 40 is preferably configured to operate such that the seventh time instant ($t_7$) is greater than the sixth time instant ($t_6$), the sixth time instant ($t_6$) is greater than the fifth time instant ($t_5$), the fifth time instant ($t_5$) is greater than the fourth time instant ($t_4$), the fourth time instant ($t_4$) is greater than the third time instant ($t_3$), the third time instant ($t_3$) is greater than the second time instant ($t_2$), the second time instant ($t_2$) is greater than the first time instant ($t_1$), and the first time instant ($t_1$) is greater than the initial time. Moreover, the fourth time instant ($t_4$) is substantially equal to the third time instant ($t_3$). Furthermore, the fifth time instant ($t_5$) and/or the seventh time instant ($t_7$) are preferably within five (5) seconds of the sixth time instant ($t_6$), more preferably within two (2) seconds of the sixth time instant ($t_6$), and even more preferably within one (1) second of the sixth time instant ($t_6$).

Figure 5:
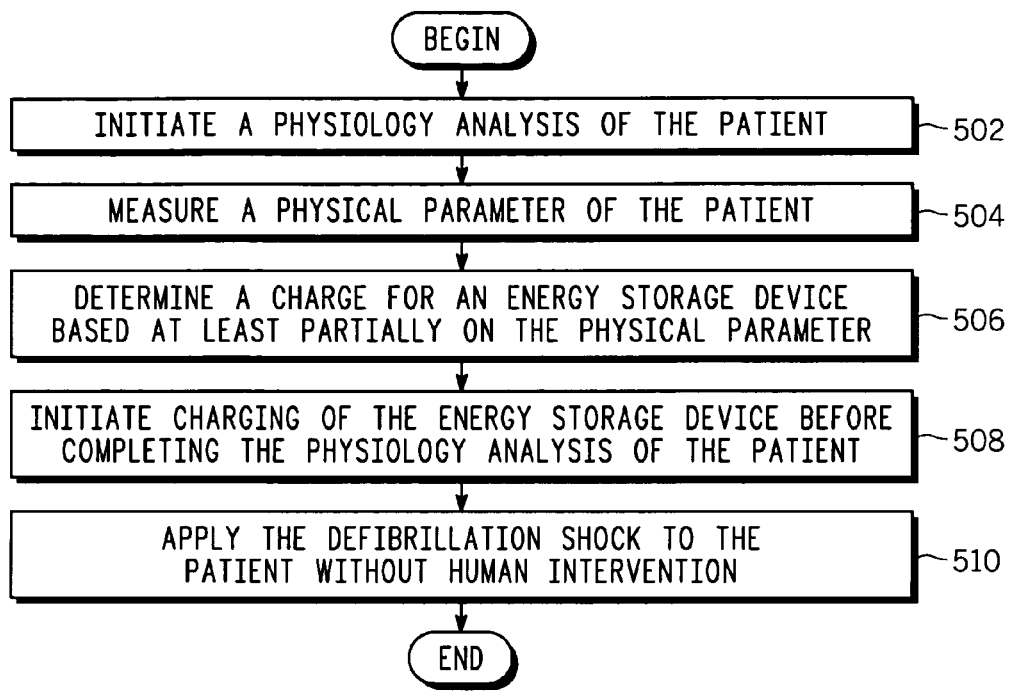
FIG. 5 is a flowchart for the method of operating the external defibrillator of FIG. 2 in accordance with a second exemplary embodiment of the present invention.

Referring to FIG. 5, a flowchart is presented that illustrates a method 500 of operating the external defibrillator in accordance with a second exemplary embodiment of the present invention. The method 500 begins by initiating a physiology analysis of the patient 502 and measuring a physical parameter of the patient 504. A charge for the energy storage device is determined based at least partially on the physical parameter 506 and the charging of the energy storage devices is initiated 506 after initiating the physiology analysis of the patient 502 and before the completion of the physiology analysis 508. Lastly, the defibrillation shock is applied to the patient without human intervention 510 (i.e., an automatic or automated activity).

Figure 6:
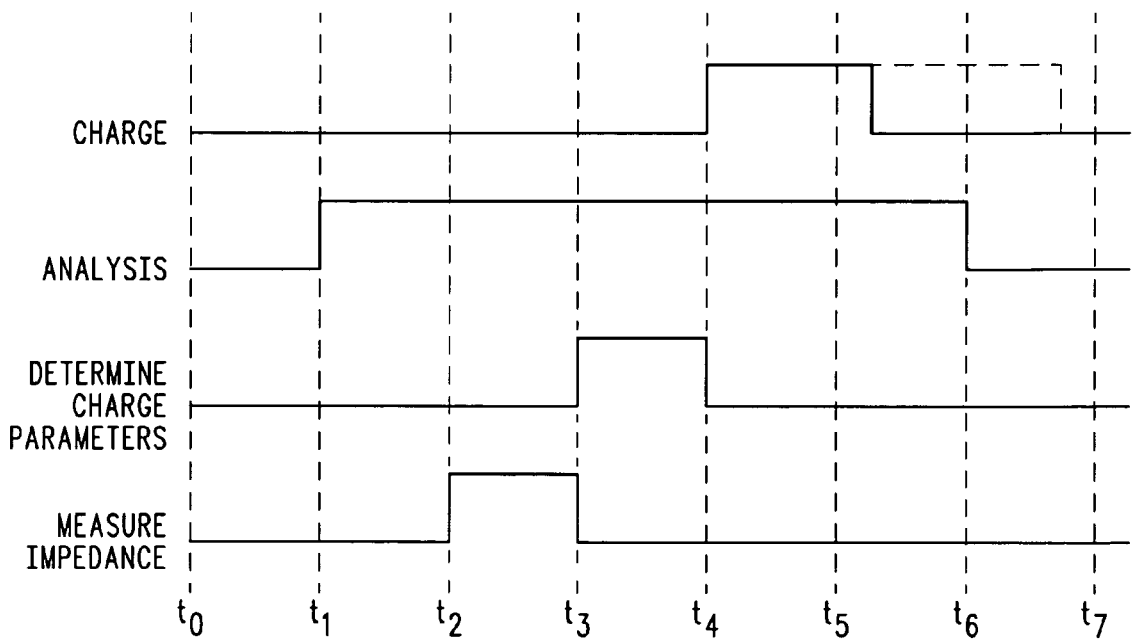
FIG. 6 is an exemplary timing diagram for operating the external defibrillator of FIG. 2 in accordance with the second exemplary embodiment of the present invention.

Referring to FIG. 6, a timing diagram 56 is presented that illustrates an example with greater detail for the operating of the external defibrillator in accordance with the second exemplary embodiment illustrated in FIG. 5. Referring to FIG. 6 in conjunction with continuing reference to FIG. 2, a timing diagram 56 is presented that illustrates the charging of the one or more energy storage devices 50 of the external defibrillator 24 in accordance with a second exemplary embodiment of the present invention. While the events presented in the timing diagram are shown as beginning and ending at the same time instant, it should be appreciated that delays can exist and the events do not need to begin and end at the same time instant as illustrated in FIG. 6. Rather, one event can end before or after another time event.

The external defibrillator 24 is activated at an initial time instant ($t_0$). This activation can be accomplished using any number of techniques such activation of an input switch 30 as shown in FIG. 1. After activation of the external defibrillator 24 at the initial time instant ($t_0$), a physiology analysis begins at a first time instant ($t_1$) and completes at a sixth time instant ($t_6$). As previously described in this detailed description, the physiology analysis can be any number analyses used to determine whether a defibrillation shock is preferably applied to the patient. For example, an ECG analysis can be conducted in accordance with techniques known to those of ordinary skill in the art based at least partially upon an ECG signal received by the controller 40 from the preamplifier/measuring circuit 42.

After the physiology analysis begins at the first time instant ($t_1$) and prior to completion of the physiology analysis at the sixth time instant ($t_6$), a charge of the one or more energy storage devices 50 is initiated at a fourth time instant ($t_4$). Prior to initiating the charge of the one or more energy storage devices 50 at the fourth time instant ($t_4$), one or more physical parameters of the patient are preferably measured with the one or more of the electrodes (32,34,36,38) at a second time instant ($t_2$). Any number of physical parameters can be measured in accordance with the present invention. For example, the physical parameter can be the transthoracic impedance between at least two of the electrodes (32,34,36, 38). The signal or signals associated with the one or more physical parameters are preferably provided to the preamplifier/measuring circuit 42 for preprocessing and/or amplification. The controller 40 receives the physical parameter and determines one or more charging parameters beginning at a third time instant ($t_3$). The one of the charging parameters determined by the controller 40, which is at least partially based upon the physical parameter, is the charge for the one or more energy storage devices 50 that provides the desired defibrillation shock for the patient. This determination can be accomplished using any number of techniques known to those of ordinary skill in the art.

In addition to determining the charge, the controller 40 also preferably determines a charging rate to substantially achieve the charge no less than about a fifth time instant ($t_5$) prior to completion of a physiology analysis at the sixth time instant ($t_6$). In addition, the controller 40 also preferably determines the charging rate to substantially achieve the charge no more than about a seventh time instant ($t_7$) after completion of the physiology analysis at the sixth time instant ($t_6$). The rate can be determined using any number of techniques, such as the calculation of equation (1).

After the charge and charging rate are determined, the charge of the one or more energy storage devices is substantially completed, the physiology analysis is substantially completed, which is no later than the seventh time instant ($t_7$), and if the physiology analysis indicates it is appropriate to provide a defibrillation shock to the patient, the controller 40 can be configured to automatically initiate the appropriate action(s) to couple the one or more charged energy storage device(s) 50 to the patient and/or the controller 40 can request an operator request prior to initiating the appropriate action(s) to couple the one or more charged energy storage device(s) 50 to the patient. For example, the appropriate action(s) initiated by the controller 40 to couple the one or more charged energy storage device(s) to the patient can including closing a switch 56 of the energy delivery circuit 52 to couple the one or more energy storage devices 50 to two or more of the electrodes attached to the patient.

In accordance with the controller 40 is preferably configured to operate such that the seventh time instant ($t_7$) is greater than the sixth time instant ($t_6$), the sixth time instant ($t_6$) is greater than the fifth time instant ($t_5$), the fifth time instant ($t_5$) is greater than the fourth time instant ($t_4$), the fourth time instant ($t_4$) is greater than the third time instant ($t_3$), the third time instant ($t_3$) is greater than the second time instant ($t_2$), the second time instant ($t_2$) is greater than the first time instant ($t_1$), and the first time instant ($t_1$) is greater than the initial time. Moreover, the fourth time instant ($t_4$) is preferably substantially equal to the third time instant ($t_3$). Furthermore, the fifth time instant ($t_5$) and/or the seventh time instant ($t_7$) are preferably within five (5) seconds of the sixth time instant ($t_6$), more preferably within two (2) seconds of the sixth time instant ($t_6$), and even more preferably within one (1) second of the sixth time instant ($t_6$).

Figure 7:
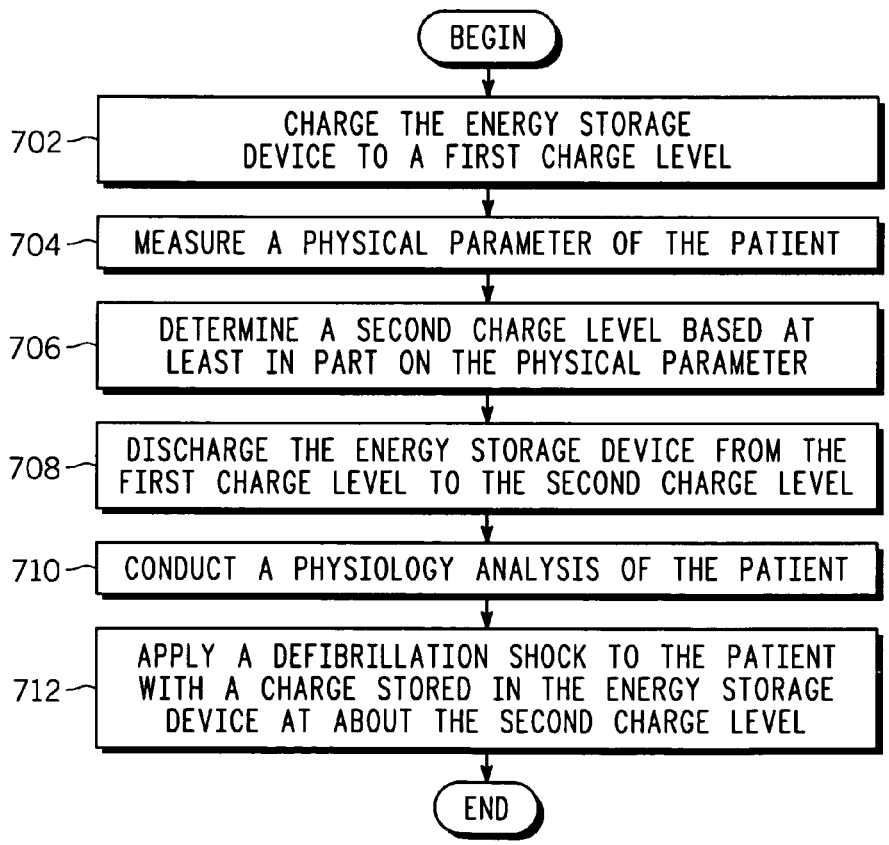
FIG. 7 is a flowchart for operating the external defibrillator of FIG. 2 in accordance with a third exemplary embodiment of the present invention.

Referring to FIG. 7, a flowchart is presented that illustrates a method 700 of operating the external defibrillator of FIG. 2 in accordance with a third exemplary embodiment of the present invention. The method 700 begins by charging an energy storage device of the external defibrillator to a first charge level 702 and measuring a physical parameter of the patient 704. A second charge level is determined based at least in part on the physical parameter of the patient 706 and the energy storage device is discharged from the first charge level to the second charge level 708. A physiology analysis of the patient is conducted 710 and the defibrillation shock is applied to the patient.

Figure 8:
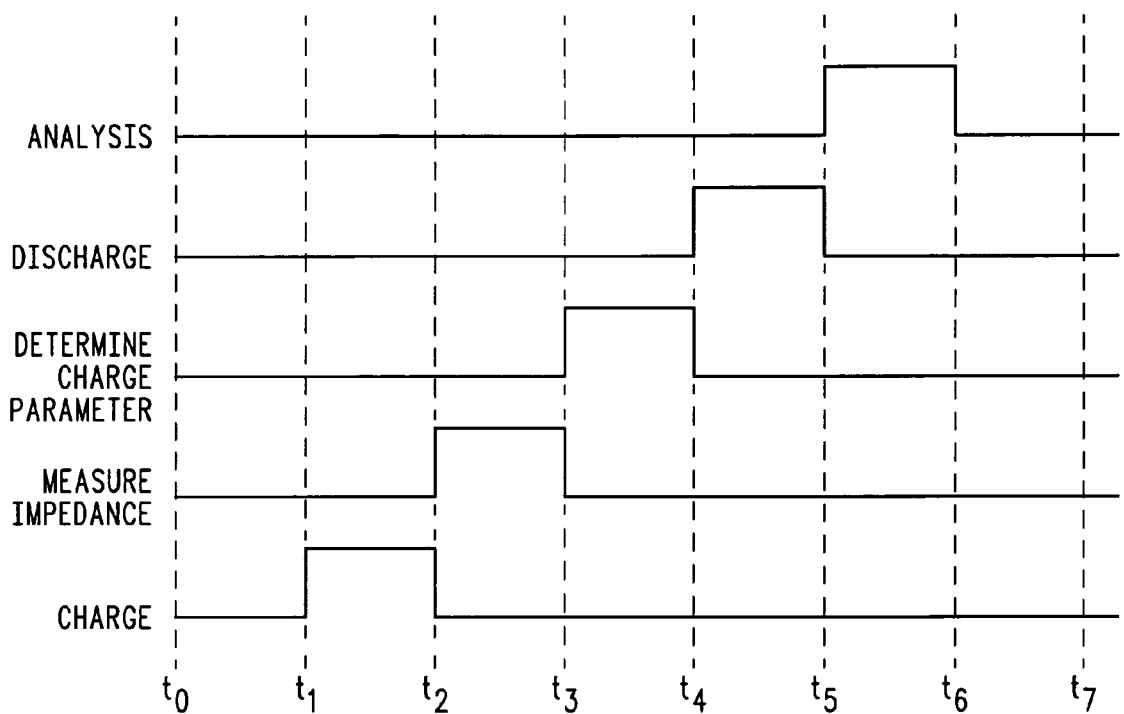
FIG. 8 is an exemplary timing diagram for operating the external defibrillator of FIG. 2 in accordance with the third exemplary embodiment of the present invention.

Referring to FIG. 8, a timing diagram 58 is presented that illustrates an example with greater detail for the operating of the external defibrillator in accordance with the third exemplary embodiment illustrated in FIG. 7. Referring to FIG. 8 in conjunction with continuing reference to FIG. 2, a timing diagram 58 is presented that illustrates the charging of the one or more energy storage devices 50 of the external defibrillator 24 in accordance with a third exemplary embodiment of the present invention. While the events presented in the timing diagram are shown as beginning and ending at the same time instant, it should be appreciated that delays can exist and the events do not need to begin and end at the same time instant as illustrated in FIG. 8. Rather, one event can end before or after another time event.

The external defibrillator 24 is activated at an initial time instant ($t_0$). This activation can be accomplished using any number of techniques such activation of an input switch 30 as shown in FIG. 1. After activation of the external defibrillator 24 at the initial time instant ($t_0$), the one or more energy storage devices 50 are charged to a first charge level at a first time instant ($t_1$). The first charge level is preferably greater than about fifty percent (50%) of the maximum charge for the one or more energy storage devices 50, more preferably greater than about seventy-five percent (75%) of the maximum charge of the one or more energy storage devices 50 and even more preferably greater than about ninety percent (90%) of the maximum charge of the one or more energy storage devices 50. After the first charge level is reached, the one or more physical parameters of the patient are preferably measured with the one or more of the electrodes (32,34,36,38) at a second time instant ($t_2$) as shown in FIG. 1.

Any number of physical parameters can be measured in accordance with the present invention. For example, the physical parameter can be the transthoracic impedance between at least two of the electrodes (32,34,36,38). The signal or signals associated with the one or more physical parameters are preferably provided to the pre-amplifier/measuring circuit 42 for preprocessing and/or amplification. The controller 40 receives the physical parameter and determines one or more charging parameters beginning at a third time instant ($t_3$). The one of the charging parameters determined by the controller 40, which is at least partially based upon the physical parameter, is the charge for the one or more energy storage devices 50 that provides the desired defibrillation shock for the patient. This determination can be accomplished using any number of techniques known to those of ordinary skill in the art.

After the one or more charging parameters are determined by the controller, the one or more energy storage devices 50 that were previously charged are discharged at a fourth time instant ($t_4$). The discharge is conducted to decrease the charge of the one or more energy storage devices 50 from the first charge level to the charge that provides the desired defibrillation shock for the patient. This discharge at the fourth time instant ($t_4$) is followed by a physiology analysis that begins at a fifth time instant ($t_5$) and completes at a sixth time instant ($t_6$). As previously described in this detailed description, the physiology analysis can be any number analyses used to determine whether a defibrillation shock is preferably applied to the patient. For example, an ECG analysis can be conducted in accordance with techniques known to those of ordinary skill in the art based at least partially upon an ECG signal received by the controller 40 from the preamplifier/measuring circuit 42.

After the physiology analysis is completed at the sixth time instant ($t_1$), the controller 40 can be configured to automatically initiate the appropriate action(s) to couple the one or more charged energy storage device(s) 50 to the patient and/or the controller 40 can request an operator request prior to initiating the appropriate action(s) to couple the one or more charged energy storage device(s) 50 to the patient if the physiology analysis indicates the desirability of such a defibrillation shock. For example, the appropriate action(s) initiated by the controller 40 to couple the one or more charged energy storage device(s) to the patient can including closing a switch 56 of the energy delivery circuit 52 to couple the one or more energy storage devices 50 to two or more of the electrodes attached to the patient.

The foregoing methods and configurations of the external defibrillator preferably provide the charge for the initial defibrillation shock after initial activation of the external defibrillator. However, additional defibrillation shocks can be provided after the initial defibrillation shock in order to return the heart rhythm to a sinus rhythm. In addition, the one or more energy storage devices can be charged and a determination can be made that a defibrillation shock is inadvisable. In such a situation, the charge in the one or more energy storage devices can be discharged into other devices such a resistor. Alternatively, the charge can be maintained for future availability if a determination is subsequently made that a defibrillation shock is advisable.

Figure 9:
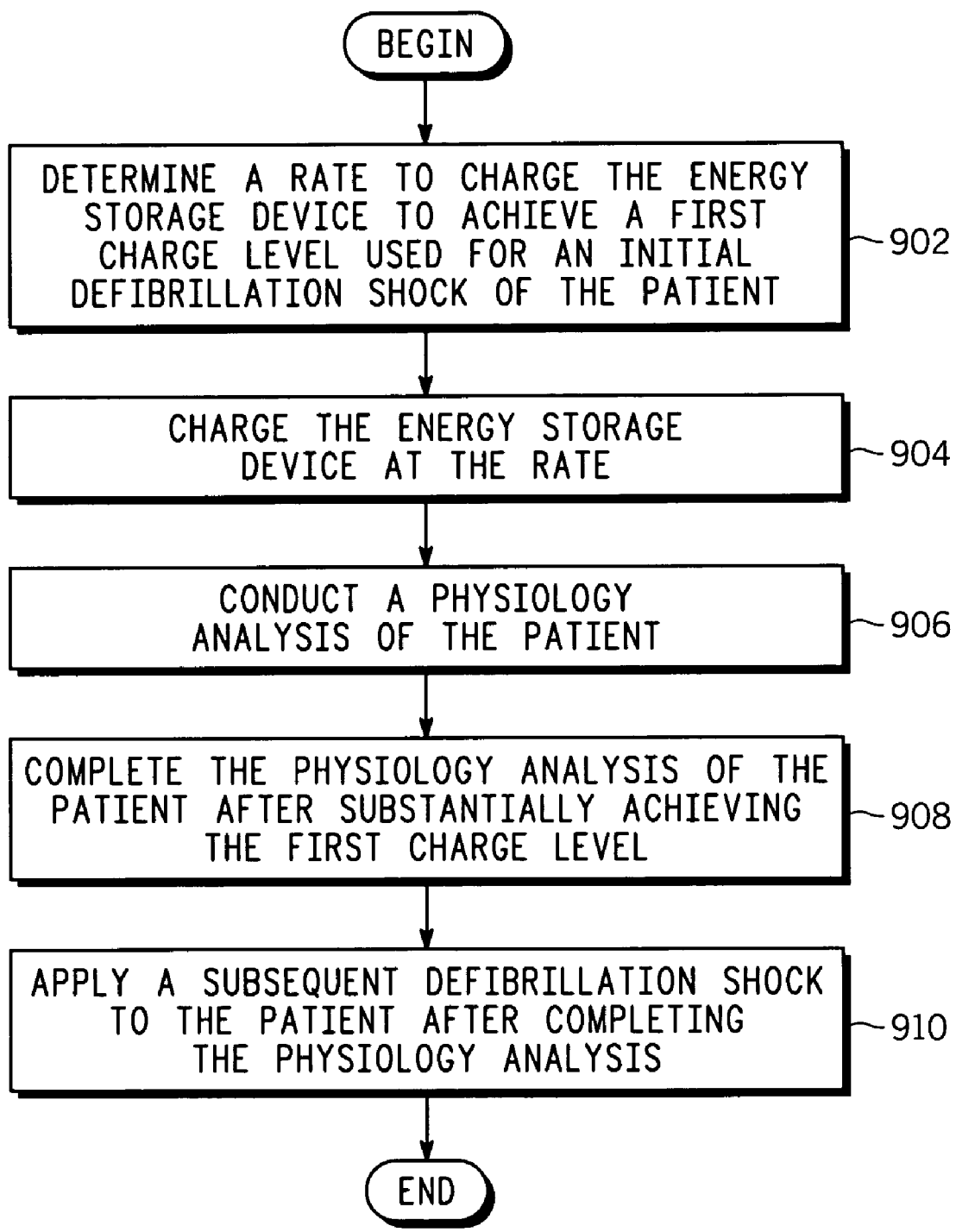
FIG. 9 is a flowchart for operating the external defibrillator of FIG. 2 in accordance with a fourth exemplary embodiment of the present invention.

Referring to FIG. 9, a flowchart is presented that illustrates a method 900 of operating the external defibrillator of FIG. 2 in accordance with a fourth exemplary embodiment of the present invention. The method 900 begins by determining a rate to charge the energy storage device to achieve a first charge level used for an initial defibrillation shock of the patient 702 and charging the energy storage device at the rate 704. A physiology analysis of the patient is conducted 906 and completed after substantially achieving the first charge level 908. Once the physiology analysis of the patient is competed 908, a subsequent defibrillation shock is applied to the patient 910.

Figure 10:
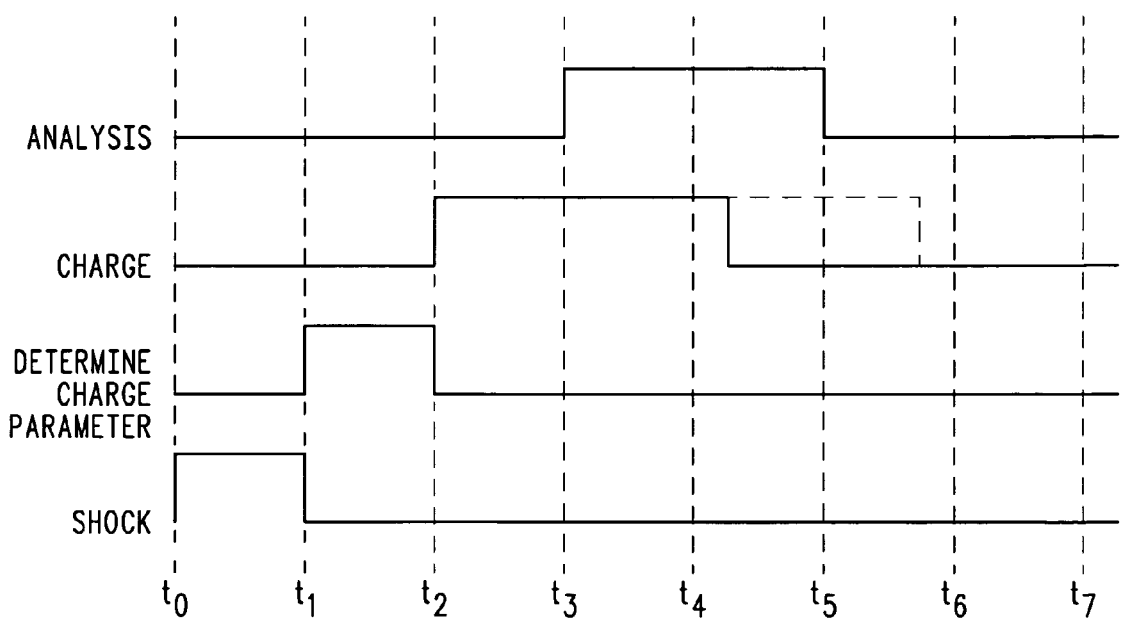
FIG. 10 is an exemplary timing diagram for operating the external defibrillator of FIG. 2 in accordance with the fourth exemplary embodiment of the present invention.

Referring to FIG. 10, a timing diagram 60 is presented that illustrates an example with greater detail for the operating of the external defibrillator 24 in after an initial defibrillation shock is provided at an initial time instant ($t_0$) in accordance with the fourth exemplary embodiment illustrated in FIG. 9. While the events presented in the timing diagram are shown as beginning and ending at the same time instant, it should be appreciated that delays can exist and the events do not need to begin and end at the same time instant as illustrated in FIG. 9. Rather, one event can end before or after another time event.

After the initial defibrillation shock is provided at the initial time instant ($t_0$) with the charge stored in the one or more energy storage, the controller 40 receives determines one or more charging parameters beginning at a first time instant ($t_1$), and preferably determines the charging rate to substantially achieve the charge of the initial defibrillation shock no less than about a fourth time instant ($t_4$) prior to completion of a physiology analysis at a fifth time instant ($t_5$), which preferably began at a third time instant ($t_3$). In addition, the controller 40 also preferably determines the charging rate to charge the one or more energy storage devices, which were discharged for the defibrillation shock ($t_2$), beginning a second time instant ($t_2$) to substantially achieve the charge of the initial defibrillation shock no more than about a sixth time instant ($t_6$) after completion of the physiology analysis at the fifth time instant ($t_5$). The rate can be determined using any number of techniques. For example the charging rate ($Q_{Rate}$) can be determined using equation (1), where $Q_{Initial}$ is charge of the one or more energy storage devices 50 after the initial defibrillation shock, $Q_{final}$ is charge of the one or more energy storage devices 50 prior to the initial defibrillation shock and $Time_{Analysis}$ is the time it takes to complete the physiology analysis, which can be the minimum time, maximum time, or average time to complete such a physiology analysis. The minimum time, maximum time or average time will vary depending upon the measurement scheme and physiology analysis conducted by the controller 40. The physiology analysis can be any number analyses used to determine whether a defibrillation shock is preferably applied to the patient. For example, an ECG analysis can be conducted in accordance with techniques known to those of ordinary skill in the art based at least partially upon an ECG signal received by the controller 40 from the preamplifier/measuring circuit 42.

After the physiology analysis and the charge is substantially completed, which is no later than the sixth time instant ($t_6$), and if the physiology analysis indicates it is appropriate to provide a defibrillation shock to the patient, the controller 40 can be configured to increase or decrease the charge level (i.e., adjust the charge level) and also configured to automatically initiate the appropriate action(s) to couple the one or more charged energy storage device(s) 50 to the patient and/or the controller 40 can request an operator request prior to initiating the appropriate action(s) to couple the one or more charged energy storage device(s) 50 to the patient. For example, the appropriate action(s) initiated by the controller 40 to couple the one or more charged energy storage device(s) to the patient can including closing a switch 56 of the energy delivery circuit 52 to couple the one or more energy storage devices 50 to two or more of the electrodes attached to the patient.

In accordance with the controller 40 is preferably configured to operate such that the sixth time instant ($t_6$) is greater than the fifth time instant ($t_5$), the fifth time instant ($t_5$) is greater than the fourth time instant ($t_4$), the fourth time instant ($t_4$) is greater than the third time instant ($t_3$), the third time instant ($t_3$) is greater than the second time instant ($t_2$), the second time instant ($t_2$) is greater than the first time instant ($t_1$), and the first time instant ($t_1$) is greater than the initial time. Moreover, the third time instant (t3) is preferably substantially equal to the second time instant ($t_2$). Furthermore, the fourth time instant ($t_4$) and/or the sixth time instant ($t_6$) are preferably within five (5) seconds of the fifth time instant ($t_5$), more preferably within two (2) seconds of the fifth time instant ($t_5$), and even more preferably within one (1) second of the fifth time instant ($t_5$).

Figure 11:
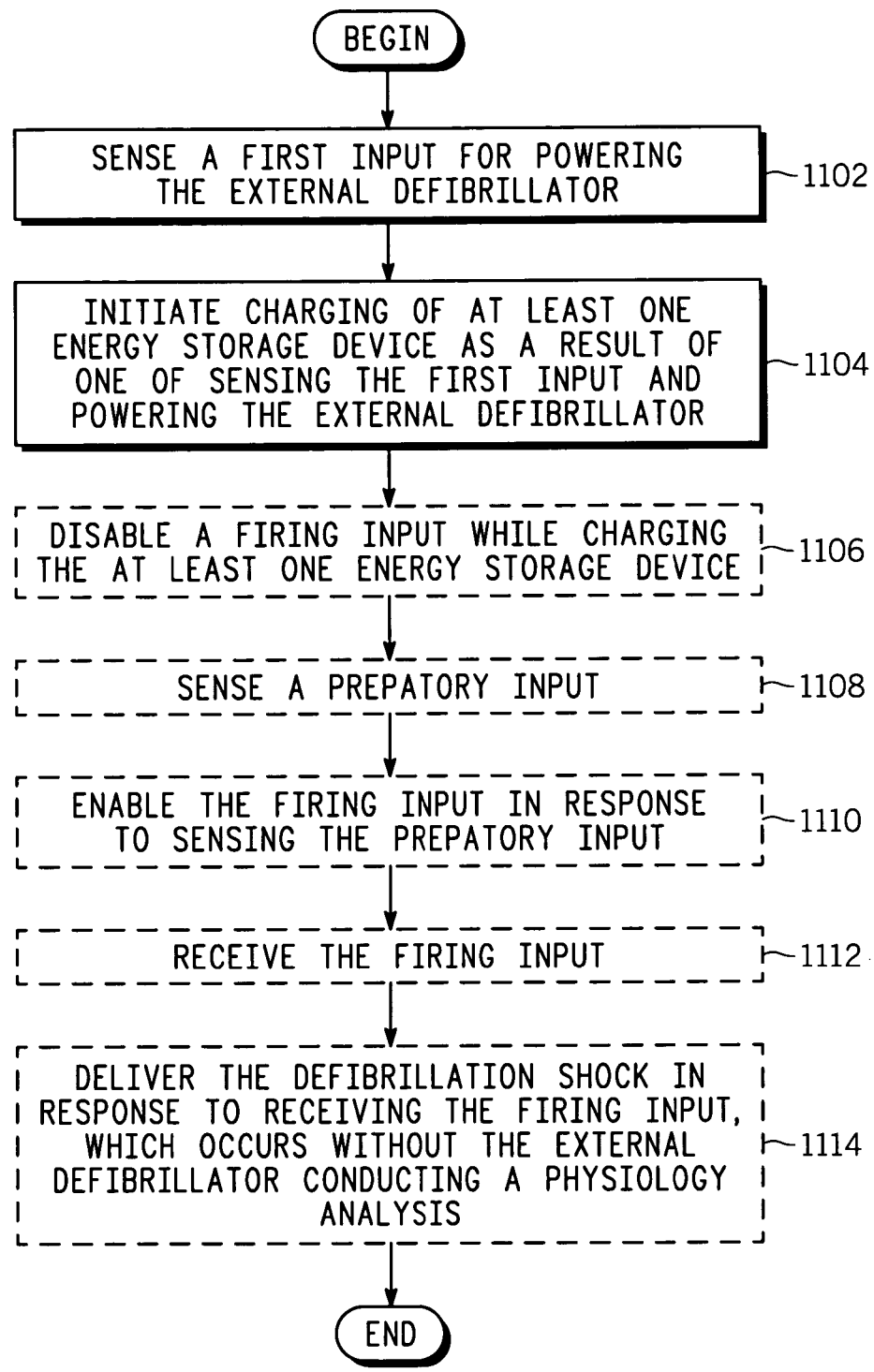
FIG. 11 is a flowchart for operating the external defibrillator of FIG. 2 in accordance with a fifth exemplary embodiment of the present invention.

Referring to FIG. 11, a flowchart is presented that illustrates a method 1100 of operating the external defibrillator of FIG. 2 in accordance with a fifth exemplary embodiment of the present invention. The method 1100 begins with sensing a first input for powering the external defibrillator 1102. The first input can be any number of inputs such as a power button of the user interface. In response to sensing the first input or in response to an initial powering up of the external defibrillator, the method 1100 initiates the charging of the energy storage devices of the external defibrillator 1104. Optionally, the method 1100 continues with the disablement of a firing input, such as a shock button of the user interface, while the charging the energy storage devices 1106. Furthermore, the method 110 optionally continues with sensing a preparatory input 1108, such as an analyze input or charge input of the user interface, and enabling the firing input in response to sensing the preparatory input 1110. The method 1100 receives the firing input that requests delivery of the defibrillation shock 1112, and delivering the defibrillation shock in response to receiving the firing input, which occurs without the external defibrillator conducting a physiology analysis of the patient 1114.

Referring to FIG. 12, a flowchart is presented that illustrates a method 1200 of operating the external defibrillator of FIG. 2 in accordance with a sixth exemplary embodiment of the present invention. The method 1200 begins with the delivery of an initial defibrillation shock 1202 and beginning to charge an energy storage device of the external defibrillator as a result of the delivery of the initial defibrillation shock and without human intervention 1204. A physiology analysis of the patient is initiated after beginning to charge the energy storage device 1206 and a subsequent defibrillation shock is delivered without human intervention after initiating the physiology analysis 1208.

Referring to FIG. 13, a flowchart is presented that illustrates a method 1300 of operating the external defibrillator of FIG. 2 in accordance with a seventh exemplary embodiment of the present invention. The method 1300 begins with an activation of the external defibrillator 1302 and sensing application of at least one of the plurality of electrodes to the patient 1304, which as known to those of ordinary skill in the art will alter an electrical property seen by the external defibrillator (e.g., a sudden increase in the impedance measured across the electrodes (e.g., twenty (20Ω) ohms to thirty ohms (300Ω) will be seen when the electrodes are attached to the patient. The method 1300 continues with the measuring a physical parameter of the patient 1306, initiating the charging of the external defibrillator to achieve an energy level for at least one energy storage device of the external defibrillator 1308, conducting a physiology analysis of the patient in order to determine a desirability for application of a defibrillation shock to the patient 1310 and delivering the defibrillation shock to the patient through the plurality of electrodes if said desirability for application of the defibrillation shock to the patient exists 1312.

In view of the foregoing, it should be appreciated that methods and apparatus are available that minimize the inherent time delay between defibrillator activation and the administration of a defibrillation shock therapy. While a finite number of exemplary embodiments have been presented in the foregoing detailed description of the invention, it should be appreciated that a vast number of variations exist. It should also be appreciated that the exemplary embodiments are only examples, and are not intended to limit the scope, applicability, or configuration of the invention in any way. Rather, the foregoing detailed description will provide those skilled in the art with a convenient road map for implementing exemplary embodiments of the invention. It being understood that various changes may be made in the function and arrangement of elements described in an exemplary embodiment without departing from the scope of the invention as set forth in the appended claims.

What is claimed is:

1. A method of operating an external defibrillator that is configured to provide a defibrillation shock to a patient, comprising the steps of:
    beginning to charge an energy storage device of the external defibrillator at an initial rate;
    initiating a physiology analysis of the patient without human intervention after said beginning to charge said energy storage device;
    determining a second rate to charge an energy storage device based at least in part upon said physiology analysis;
    charging said energy storage device at said second rate; and
    applying the defibrillation shock to the patient without human intervention after said initiating said physiological analysis of the patent.

2. The method of operating the external defibrillator that is configured to provide the defibrillation shock to the patient of claim 1, further comprising the steps of:
    if said second rate is different from said initial rate, updating said charge rate from said initial rate to said second rate.

3. The method of operating the external defibrillator that is configured to provide the defibrillation shock to the patient of claim 1, further comprising the step of determining a physical parameter of the patient.

4. The method of operating the external defibrillator that is configured to provide the defibrillation shock to the patient of claim 3, wherein said physical parameter is a transthoracic impedance.

5. The method of operating the external defibrillator that is configured to provide the defibrillation shock to the patient of claim 1, wherein said physiology analysis is a ElectroCardioGram (ECG).

6. The method of operating the external defibrillator that is configured to provide the defibrillation shock to the patient of claim 1, further comprising the step of activating the external defibrillator prior to said beginning to charge said energy storage device.

7. A method of charging an energy storage device of an external defibrillator that is configured to provide a defibrillation shock to a patient, comprising the steps of:
    measuring a physical parameter of the patient at about a first time instant ($t_1$);
    determining a charge for the energy storage device at about a second time instant ($t_2$) that is at least partially based on said physical parameter;
    completing a physiology analysis of the patient at about a sixth time instant ($t_6$);
    determining a rate for charging said energy storage device to substantially achieve said charge after about a fifth time instant ($t_5$) and before about a seventh time instant ($t_7$), said fifth time occurring before about said sixth time instant ($t_6$) and said seventh time instant ($t_7$) occurring after about said sixth time instant ($t_6$); and
    beginning to charge said energy storage device at said rate at about a third time instant ($t_3$).

8. The method of charging the energy storage device of claim 7, further comprising the step of beginning said physiology analysis of the patient at about a fourth time instant ($t_4$).

9. The method of charging the energy storage device of claim 8, further comprising the step of activating said external defibrillator at an initial time instant ($t_0$).

10. The method of charging the energy storage device of claim 9, wherein said seventh time instant ($t_7$) is later than said sixth time instant ($t_6$), said sixth time instant ($t_6$) is later than said fifth time instant ($t_5$), said fifth time instant ($t_5$) is later than said fourth time instant ($t_4$), said fourth time instant ($t_4$) is later than said third time instant ($t_3$), said third time instant ($t_3$) is later than said second time instant ($t_2$) said second time instant ($t_2$) is later than said first time instant ($t_1$), and said first time instant ($t_1$) is later than said initial time instant ($t_0$).

11. The method of charging the energy storage device of claim 9, wherein said fourth time instant ($t_4$) is substantially equal to said third time instant ($t_3$).

12. The method of charging the energy storage device of claim 7, wherein said physical parameter is a transthoracic impedance.

13. The method of charging the energy storage device of claim 7, wherein said physiology analysis is an ElectroCardioGram (ECG) analysis.

14. The method of charging the energy storage device of claim 7, wherein said fifth time instant ($t_5$) is within about two (2) seconds of said sixth time instant ($t_6$).

15. The method of charging the energy storage device of claim 7, wherein said seventh time instant ($t_7$) is within about two (2) seconds of said sixth time instant ($t_6$).

16. A method of charging an energy storage device of an external defibrillator that is configured to provide a defibrillation shock to a patient, comprising the steps of:
   initiating a physiology analysis of the patient;
   completing said physiology analysis of the patient;
   initiating a charge of said energy storage device after said initiating said physiology analysis and before said completing said physiology analysis;
   measuring a physical parameter of the patient;
   determining a rate for charging said energy storage device after said measuring said physical parameter of the patient to substantially complete said charging at a desired point in time, wherein said rate of charging is at least partially based on said physical parameter; and
   applying the defibrillation shock to the patient without human intervention.

17. The method of charging the energy storage device of claim 16, further comprising the step of activating said external defibrillator at an initial time instant ($t_0$).

18. The method of charging the energy storage device of claim 16, wherein said physical parameter is a transthoracic impedance.

19. The method of charging the energy storage device of claim 16, wherein said physiology analysis is a ECG analysis.

20. The method of charging the energy storage device of claim 16, wherein step of determining a charge rate is within about two (2) seconds of the step of completing said physiology analysis.

21. The method of charging the energy storage device of claim 16, wherein the step of applying the defibrillation shock is within about two (2) seconds of the step of determining a charge rate.

22. A method of operating an external defibrillator that is configured to provide a defibrillation shock to a patient, comprising the steps of:
   beginning to charge an energy storage device of the external defibrillator at an initial rate;
   initiating a physiology analysis of the patient after said beginning to charge said energy storage device; and
   determining a rate to charging an energy storage device based at least in part upon said physiology analysis;
   charging said energy storage device at said determined rate; and
   applying the defibrillation shock to the patient after said initiating said physiological analysis of the patent.

23. The method of operating the external defibrillator of claim 22, further comprising the steps of:
   if said determined rate is different from said initial rate, updating said charge rate from said initial rate to said determined rate.

24. The method of operating the external defibrillator of claim 22, further comprising the step of determining a physical parameter of the patient.

25. The method of operating the external defibrillator of claim 24, wherein said physical parameter is a transthoracic impedance.

26. The method of operating the external defibrillator of claim 22, wherein said physiology analysis is an ECG analysis.

27. The method of operating the external defibrillator of claim 22, further comprising the step of activating the external defibrillator prior to the step of beginning to charge said energy storage device.

28. The method of claim 22 wherein the defibrillator is a manual defibrillator.

29. A method of charging an energy storage device of an external defibrillator that is configured to provide a defibrillation shock to a patient, comprising the steps of:
   initiating a physiology analysis of the patient;
   completing said physiology analysis of the patient;
   initiating a charge of said energy storage device after said initiating said physiology analysis and before said completing said physiology analysis;
   measuring a physical parameter of the patient;
   determining a rate for charging said energy storage device after said measuring said physical parameter of the patient to substantially complete said charging at a desired point in time, wherein said rate of charging is at least partially based on said physical parameter; and
   applying the defibrillation shock to the patient.

30. The method of charging the energy storage device of claim 29, further comprising the step of activating said external defibrillator at an initial time instant ($t_0$).

31. The method of charging the energy storage device of claim 29, wherein said physical parameter is a transthoracic impedance.

32. The method of charging the energy storage device of claim 29, wherein said physiology analysis is a ECG analysis.

33. The method of charging the energy storage device of claim 29, wherein the step of determining a charge rate is within about two (2) seconds of the step of completing said physiology analysis.

34. The method of charging the energy storage device of claim 29, wherein the step of applying the defibrillation shock is within about two (2) seconds of the step of determining a charge rate.

35. The method of claim 29 wherein the defibrillator is a manual defibrillator.

* * * * *

UNITED STATES PATENT AND TRADEMARK OFFICE
CERTIFICATE OF CORRECTION

PATENT NO. : 7,242,979 B1 Page 1 of 1
APPLICATION NO. : 10/622868
DATED : July 10, 2007
INVENTOR(S) : Kelly et al.

It is certified that error appears in the above-identified patent and that said Letters Patent is hereby corrected as shown below:

On the title page, in Item (57), under "Abstract", column 2, line 5, after "one or" insert -- more --.

In Sheet 7 of 8, Box 1108, FIG. 11, line 1, delete "PREPATORY" and insert -- PREPARATORY --, therefor.

In Sheet 7 of 8, Box 1110, FIG. 11, line 2, delete "PREPATORY" and insert -- PREPARATORY --, therefor.

In column 10, line 31, delete "(t3)" and insert -- $t_3$ --, therefor.

In column 11, line 59, in Claim 1, delete "patent" and insert -- patient --, therefor.

In column 13, line 27, in Claim 20, after "wherein" insert -- the --.

In column 13, line 46, in Claim 22, delete "patent" and insert -- patient --, therefor.

Signed and Sealed this

Seventeenth Day of November, 2009

David J. Kappos
*Director of the United States Patent and Trademark Office*